United States Patent
Chen et al.

(10) Patent No.: US 12,232,896 B2
(45) Date of Patent: Feb. 25, 2025

(54) METHOD AND APPARATUS FOR DETERMINING TARGET LOCATION OF SINGLE-SLOT COLLIMATING PLATE AND COLLIMATOR ASSEMBLY

(71) Applicant: Siemens Shanghai Medical Equipment Ltd., Shanghai (CN)

(72) Inventors: Wen Hao Chen, Shanghai (CN); Tao Tao Li, Shanghai (CN); Yi Tian, Shanghai (CN); Jing Ming Zheng, Shanghai (CN); Chang Qing Teng, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 254 days.

(21) Appl. No.: 18/001,132

(22) PCT Filed: Jun. 10, 2020

(86) PCT No.: PCT/CN2020/095439
§ 371 (c)(1),
(2) Date: Dec. 8, 2022

(87) PCT Pub. No.: WO2021/139088
PCT Pub. Date: Jul. 15, 2021

(65) Prior Publication Data
US 2023/0210480 A1    Jul. 6, 2023

(51) Int. Cl.
*A61B 6/40*    (2024.01)
*A61B 6/03*    (2006.01)

(52) U.S. Cl.
CPC ............... *A61B 6/40* (2013.01); *A61B 6/032* (2013.01)

(58) Field of Classification Search
CPC ........... A61B 6/40; A61B 6/032; A61B 6/582; A61B 6/585; A61B 6/06
See application file for complete search history.

(56) References Cited

U.S. PATENT DOCUMENTS

| 7,046,768 | B1 | 5/2006 | Gilevich |
| 10,314,553 | B2 * | 6/2019 | Ikhlef ............... A61B 6/583 |
| 2010/0086104 | A1 | 4/2010 | Michaelsen et al. |

FOREIGN PATENT DOCUMENTS

| CN | 101919700 A | 12/2010 |
| CN | 207489501 U | 6/2018 |

(Continued)

OTHER PUBLICATIONS

Feb. 9, 2021 (PCT) International Search Report—App. PCT/CN2020/095439.

*Primary Examiner* — David P Porta
*Assistant Examiner* — Meenakshi S Sahu
(74) *Attorney, Agent, or Firm* — Banner & Witcoff Ltd.

(57) ABSTRACT

A target position determination of a single-slot collimating plate and a collimator assembly are disclosed. A first measurement signal is acquired based upon of the first instance of air scanning, when the single-slot collimating plate moves a predetermined distance from a starting position to a first position in a first direction of the Z axis. A second measurement signal is acquired based upon the second instance of air scanning, when the single-slot collimating plate moves a predetermined distance from the starting position to a second position in the direction opposite to the first direction. A composite measurement signal and a composite air calibration signal are determined based upon the first measurement signal and the second measurement signal. The composite measurement signal is calibrated using the composite air calibration signal. The target position of the single-slot collimating plate is determined based upon the calibrated composite measurement signal.

15 Claims, 6 Drawing Sheets

(56) References Cited

FOREIGN PATENT DOCUMENTS

| | | |
|---|---|---|
| CN | 109431534 A | 3/2019 |
| CN | 109770935 A | 5/2019 |
| CN | 109893153 A | 6/2019 |
| DE | 102011080607 A1 | 2/2013 |
| JP | H09038074 A | 2/1997 |
| JP | 6322164 B2 | 5/2018 |
| WO | 2020029148 A1 | 2/2020 |

* cited by examiner

METHOD AND APPARATUS FOR DETERMINING TARGET LOCATION OF SINGLE-SLOT COLLIMATING PLATE AND COLLIMATOR ASSEMBLY

TECHNICAL FIELD

The present disclosure relates to the field of medical device technologies, and in particular, to a method and an apparatus for determining a target location of a single-slot collimating plate, a collimator assembly, a control host of a CT system, and a computer readable storage medium.

BACKGROUND

In computed tomography (CT), accurate collimation X rays and highly sensitive detectors are used to scan a part of a human body. A collimator is an apparatus for limiting an X-ray irradiation direction and determining a size of an irradiation field, which can greatly reduce interference of scattered rays and limit the X-rays to a required area. Therefore, the collimator can improve image quality and reduce radiation dose to a patient. Collimators in CT usually include X-ray source-side collimators and detector-side collimators. The location of the X-ray source-side collimator plays a significant role in image quality.

Currently, the X-ray source-side collimator generally uses a multi-slot structure. In a factory tuning up phase, air scanning needs to be performed multiple times to determine the locations of the multiple slots. Tuning up is time-consuming and complex.

The industry has been committed to finding simple and convenient collimators and tuning up solutions. For example, Chinese Patent Application No. 201110081593.5 discloses a Z collimator. The Z collimator includes two rotatable collimating plates in a Z direction. Each collimating plate includes a plurality of collimating feet of different lengths, and collimating feet of the same length in the two collimating plates form a collimating foot pair by means of rotation, so as to perform collimation.

SUMMARY

A main objective of embodiments of the present disclosure is to provide a method and an apparatus for determining a target location of a single-slot collimating plate, and a collimator assembly. Embodiments of the present disclosure are further intended to propose a control host of a CT system and a computer readable storage medium.

The technical solutions of the embodiments of the present disclosure are implemented as follows:

A method for determining a target location of a single-slot collimating plate includes:
  acquiring a first measurement signal collected based on the first time of air scanning when a single-slot collimating plate moves from a start location to a first location by a predetermined distance along a first direction of a Z-axis;
  acquiring a second measurement signal collected based on the second time of air scanning when the single-slot collimating plate moves from the start location to a second location by the predetermined distance along an opposite direction of the first direction;
  determining a combined measurement signal and a combined air calibration signal based on the first measurement signal and the second measurement signal;
  calibrating the combined measurement signal by using the combined air calibration signal; and
  determining a target location of the single-slot collimating plate based on the calibrated combined measurement signal.

It can be learned that, in this embodiment of the present disclosure, a single-slot collimating plate is used, a calibrated combined measurement signal can be obtained by only performing air scanning at two slots, and a target location of the single-slot collimating plate can be quickly calculated based on the calibrated combined measurement signal. Compared with a defect in the prior art (i.e. air scanning needs to be performed multiple times by a collimator that uses a multi-slot structure), this embodiment of the present disclosure reduces a quantity of times of air scanning, and has an advantage of being more efficient, simple, and convenient.

In an embodiment, the determining a combined measurement signal and a combined air calibration signal based on the first measurement signal and the second measurement signal includes:
  determining a demarcation point between the first measurement signal and the second measurement signal;
  combining a first signal segment that is in the second measurement signal and that extends from the demarcation point along the first direction of the Z-axis with a second signal segment that is in the first measurement signal and that extends from the demarcation point along the opposite direction into the combined measurement signal; and
  combining a third signal segment that is in the first measurement signal and that extends from the demarcation point along the first direction of the Z-axis with a fourth signal segment that is in the second measurement signal and that extends from the demarcation point along the opposite direction into the combined air calibration signal.

Therefore, in this embodiment of the present disclosure, the combined measurement signal and the combined air calibration signal can be conveniently combined based on the first measurement signal and the second measurement signal.

In an embodiment, the determining a target location of the single-slot collimating plate based on the calibrated combined measurement signal includes:
  determining a center of gravity of the calibrated combined measurement signal; and
  determining the target location of the single-slot collimating plate based on the center of gravity.

It can be learned that, in this embodiment of the present disclosure, by determining the center of gravity of the calibrated combined measurement signal, the target location of the single-slot collimating plate can be quickly determined. In an embodiment, the determining a center of gravity of the calibrated combined measurement signal includes:
  determining a left channel group, a right channel group, and a middle channel group between the left channel group and the right channel group based on a channel number sequence, and determining a first average signal of a calibrated combined measurement signal of each channel in the middle channel group; and
  determining a center of gravity of the first average signal; and
  the determining the target location of the single-slot collimating plate based on the center of gravity includes: determining a Z-location offset of the single-slot collimating plate based on the center of gravity of the first average signal.

Therefore, in this embodiment of the present disclosure, an accurate optimal Z-location offset can be calculated based on the center of gravity of the first average signal of the calibrated combined measurement signal of each channel in the middle channel group, so that a Z-location of the single-slot collimating plate is subsequently precisely tuned up.

In an embodiment, the determining a center of gravity of the calibrated combined measurement signal further includes:
  determining a second average signal of a calibrated combined measurement signal of each channel in the left channel group;
  determining a center of gravity of the second average signal;
  determining a third average signal of a calibrated combined measurement signal of each channel in the right channel group; and
  determining a center of gravity of the third average signal; and
  the determining the target location of the single-slot collimating plate based on the center of gravity further includes: determining parallelism of the single-slot collimating plate based on the center of gravity of the second average signal and the center of gravity of the third average signal.

Therefore, in this embodiment of the present disclosure, an accurate optimal parallelism can be calculated based on the center of gravity of the second average signal and the center of gravity of the third average signal, so that the parallelism of the single-slot collimating plate is subsequently accurately tuned up. In an embodiment, the method further includes:
  determining curvature of the single-slot collimating plate based on the center of gravity of the second average signal, the center of gravity of the third average signal, and the center of gravity of the first average signal; and
  when the curvature is greater than a predetermined curvature threshold, sending alarm information indicating to replace the single-slot collimating plate.

Therefore, in this embodiment of the present disclosure, the curvature of the single-slot collimating plate can be calculated based on the center of gravity of the second average signal and the center of gravity of the third average signal, and when the calculated curvature exceeds the threshold, alarm information is sent to remind a user to replace the single-slot collimating plate.

An apparatus for determining a target location of a single-slot collimating plate includes:
  a first acquiring module, configured to acquire a first measurement signal collected based on the first time of air scanning when a single-slot collimating plate moves from a start location to a first location by a predetermined distance along a first direction of a Z-axis;
  a second acquiring module, configured to acquire a second measurement signal collected based on the second time of air scanning when the single-slot collimating plate moves from the start location to a second location by the predetermined distance along an opposite direction of the first direction;
  a first determining module, configured to determine a combined measurement signal and a combined air calibration signal based on the first measurement signal and the second measurement signal;
  a calibration module, configured to calibrate the combined measurement signal by using the combined air calibration signal; and
  a second determining module, configured to determine a target location of the single-slot collimating plate based on the calibrated combined measurement signal.

It can be learned that, in this embodiment of the present disclosure, a single-slot collimating plate is used, a calibrated combined measurement signal can be obtained by only performing air scanning at two slots, and a target location of the single-slot collimating plate can be quickly calculated based on the calibrated combined measurement signal. Compared with a defect in the prior art that the air scanning needs to be performed multiple times by a collimator that uses a multi-slot structure, this embodiment of the present disclosure reduces a quantity of times of air scanning, and has an advantage of being more efficient, simple, and convenient.

In an embodiment, the first determining module is configured to: determine a demarcation point between the first measurement signal and the second measurement signal; combine a first signal segment that is in the second measurement signal and that extends from the demarcation point along the first direction of the Z-axis with a second signal segment that is in the first measurement signal and that extends from the demarcation point along the opposite direction into the combined measurement signal; and combine a third signal segment that is in the first measurement signal and that extends from the demarcation point along the first direction of the Z-axis with a fourth signal segment that is in the second measurement signal and that extends from the demarcation point along the opposite direction into the combined air calibration signal.

Therefore, in this embodiment of the present disclosure, the combined measurement signal and the combined air calibration signal can be conveniently combined based on the first measurement signal and the second measurement signal.

In an embodiment, the second determining module is configured to: determine a center of gravity of the calibrated combined measurement signal, and determine the target location of the single-slot collimating plate based on the center of gravity.

It can be learned that, in this embodiment of the present disclosure, by determining the center of gravity of the calibrated combined measurement signal, the target location of the single-slot collimating plate can be quickly determined.

In an embodiment, the second determining module is configured to: determine a left channel group, a right channel group, and a middle channel group between the left channel group and the right channel group based on a channel number sequence; determine a first average signal of a calibrated combined measurement signal of each channel in the middle channel group; determine a center of gravity of the first average signal; and determine a Z-location offset of the single-slot collimating plate based on the center of gravity of the first average signal.

Therefore, in this embodiment of the present disclosure, an accurate optimal Z-location offset can be calculated based on the center of gravity of the first average signal of the calibrated combined measurement signal of each channel in the middle channel group, so that a Z-location of the single-slot collimating plate is subsequently precisely tuned up.

In an embodiment, the second determining module is further configured to: determine a second average signal of a calibrated combined measurement signal of each channel in the left channel group; determine a center of gravity of the second average signal; determine a third average signal of a calibrated combined measurement signal of each channel in the right channel group; determine a center of gravity of the third average signal; and determine parallelism of the single-slot collimating plate based on the center of gravity of the second average signal and the center of gravity of the third average signal.

Therefore, in this embodiment of the present disclosure, an accurate optimal parallelism can be calculated based on the center of gravity of the second average signal and the center of gravity of the third average signal, so that the parallelism of the single-slot collimating plate is subsequently accurately tuned up.

In an embodiment, the second determining module is further configured to determine curvature of the single-slot collimating plate based on the center of gravity of the second average signal, the center of gravity of the third average signal, and the center of gravity of the first average signal; and the apparatus further includes:

an alarm module, configured to: when the curvature is greater than a predetermined curvature threshold, send alarm information indicating to replace the single-slot collimating plate.

Therefore, in this embodiment of the present disclosure, the curvature of the single-slot collimating plate can be calculated based on the center of gravity of the second average signal and the center of gravity of the third average signal, and when the calculated curvature exceeds the threshold, alarm information is sent to remind a user to replace the single-slot collimating plate.

A collimator assembly includes:
a frame, adapted to be disposed on a rotating carrier;
a single-slot collimating plate, disposed in the frame;
a rotational fulcrum, fixed at a first end of the frame; and
a spring, disposed between an opposite end of the first end of the frame and the rotating carrier;
where the single-slot collimating plate includes a recess, and the frame has a rotational degree of freedom around the rotational fulcrum; and
the single-slot collimating plate is adapted to be moved to a target location based on a rotation process of the frame around the rotational fulcrum or a process of filling the recess with a gasket, and the target location is determined by using the method above.

It can be learned that this embodiment of the present disclosure further provides a collimator assembly that can facilitate location tuning up. By rotating the frame around the rotational fulcrum, parallelism of the single-slot collimating plate can be conveniently tuned up. By filling the recess with the gasket, a Z location of the single-slot collimating plate can be conveniently tuned up.

A collimator assembly includes:
a frame, adapted to be arranged on a rotating carrier, the frame being arranged with a first slot and a second slot arranged in parallel along a Z-axis direction;
a single-slot collimating plate, disposed in the frame;
a first spring, where a first end of the first spring is fixed to the frame, and a second end of the first spring is in contact with a sidewall of the single-slot collimating plate; and
a second spring, where a first end of the second spring is fixed to the frame, and a second end of the second spring is in contact with the sidewall;
where a first end of the single-slot collimating plate has a moving degree of freedom along the first slot, and an opposite end of the first end of the single-slot collimating plate has a moving degree of freedom along the second slot; and the single-slot collimating plate is adapted to move to a target location based on combined movement of the first end of the single-slot collimating plate along the first slot and the opposite end of the first end of the single-slot collimating plate along the second slot, movement of the first end of the single-slot collimating plate along the first slot, or movement of the opposite end of the first end of the single-slot collimating plate along the second slot, where the target location is determined by using the method above.

It can be learned that an embodiment of the present disclosure further provides a collimator assembly that facilitates location tuning up. The target location of the single-slot collimating plate can be conveniently tuned up by separately moving the first end of the single-slot collimating plate, the second end of the single-slot collimating plate, or moving the first end and the second end of the single-slot collimating plate together.

A control host of a CT system includes a memory and a processor; where the memory stores an application program capable of being executed by the processor, so that the processor performs the method according to any one of the foregoing.

Therefore, this embodiment of the present disclosure further proposes a control host that can quickly determine a target location of a single-slot collimating plate.

A computer readable storage medium, where the computer readable storage medium stores a computer program, and the computer program is executed by a processor to implement the method according to any one of the foregoing.

Therefore, this embodiment of the present disclosure further provides a computer readable storage medium that can quickly determine a target location of a single-slot collimating plate.

Figure 1:
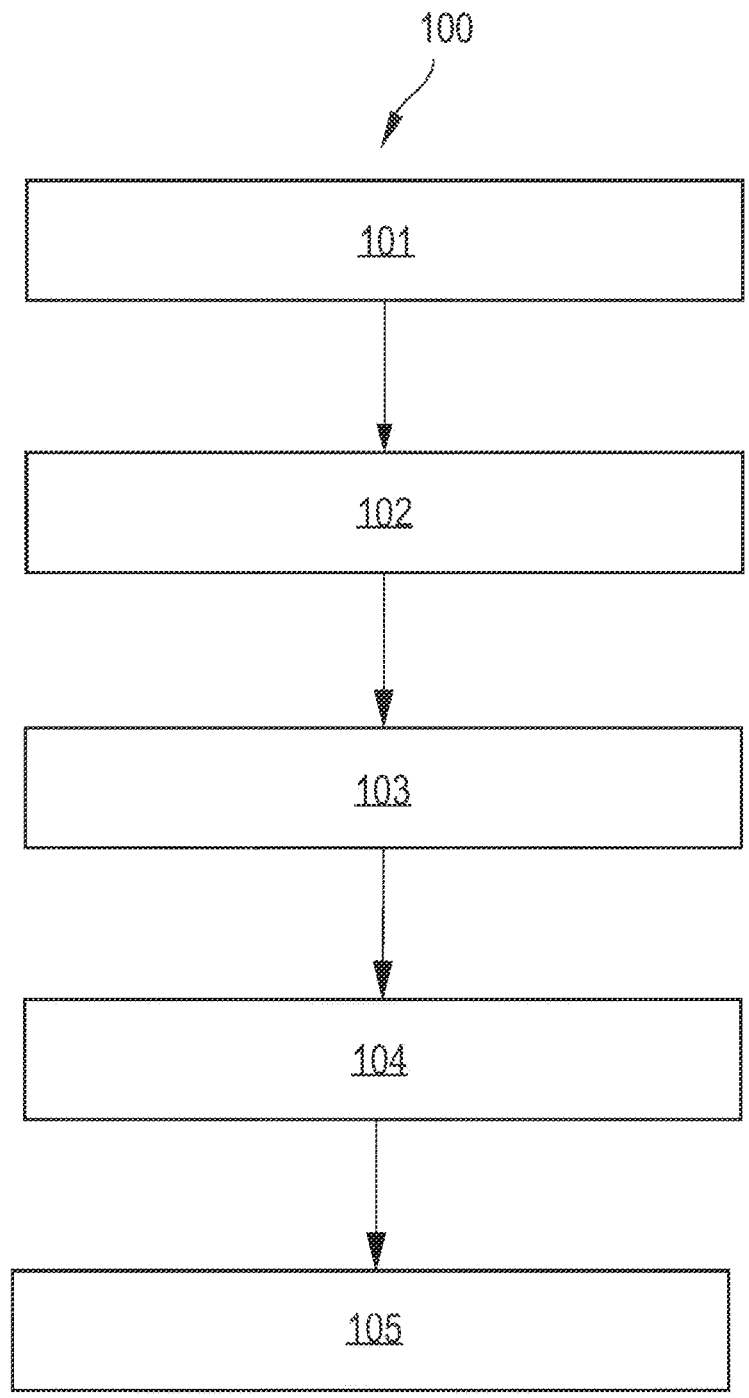
FIG. 1 is a flowchart of an example method for determining a target location of a single-slot collimating plate according to an embodiment of the present disclosure.

A list of reference numerals is as follows:

| Reference sign | Meaning |
| --- | --- |
| 100 | Method for determining a target location of a single-slot collimating plate |
| 101-105 | Steps |
| 10 | Slot plate at an initial − shift location in a Z-axis direction |
| 11 | Slot plate at an initial + shift location in a Z-axis direction |
| 12-15 | X-ray |
| 16 | Second signal segment |
| 17 | First signal segment |
| 18 | Fourth signal segment |
| 19 | Third signal segment |
| 40 | Focal point |
| 50 | Detector array |
| 70 | First signal |
| 80 | Second signal |
| 90 | Calibrated combined measurement signal |
| 20 | Collimator assembly |
| 21 | Frame |
| 22 | Rotating carrier |
| 23 | Single-slot collimating plate |
| 24 | Rotational fulcrum |
| 25 | Spring |
| 26 | Recess |
| 27 | Handle |
| 28 | Locating pin |
| 29 | Fixing bolt |
| 40 | Micrometer caliper |
| 30 | Collimator assembly |
| 31 | Frame |
| 33 | First slot |
| 34 | Second slot |
| 35 | First spring |
| 36 | Second spring |
| 37 | Single-slot collimating plate |
| 41 | First micrometer caliper |
| 42 | Second micrometer caliper |
| 800 | Apparatus for determining a target location of a single-slot collimating plate |
| 801 | First acquiring module |
| 802 | Second acquiring module |
| 803 | First determining module |
| 804 | Calibration module |
| 805 | Second determining module |
| 806 | Alarm module |
| 900 | Control host of a CT system |
| 901 | Memory |
| 902 | Processor |

DETAILED DESCRIPTION

To make technical solutions and advantages of the present disclosure clearer and more understandable, the present disclosure is further described in detail below with reference to the accompanying drawings and embodiments. It should be understood that the specific embodiments herein are merely provided for describing the present disclosure and not intended to limit the protection scope of the present disclosure.

For concise and intuitive descriptions, solutions of this disclosure are stated below by using several representative embodiments. A large quantity of details in the embodiments is merely used for helping understand the solutions of this disclosure. However, obviously, embodiment of the technical solutions of the present disclosure may be not limited to these details. To avoid unnecessarily blurring the solutions of this disclosure, some embodiments are not described in detail, but only frames are provided. In the following, "comprise" refers to "comprise, but is not limited to", and "according to . . . " refers to "at least according to . . . , but not limited to only according to . . . ".

The applicant finds that in the prior art, an X-ray source-side collimator generally uses a multi-slot structure. Therefore, in factory tuning up phase, air scanning needs to be performed multiple times (for example, at least seven times) to determine the locations of slots, and this tuning up process is time-consuming and complex. In addition, in the prior art, an additional mechanical motor or control component is further required to assist in tuning up the slot, which further increases complexity and increases production cost.

Considering the tuning up complexity of the multi-slot structure, in an embodiment of the present disclosure, a single-slot collimator including a single-slot collimating plate is used to replace the multi-slot collimator, thereby reducing complexity of tuning up process. In addition, in the embodiment of the present disclosure, a target location is determined based on center of gravity calculation of a signal, which may further ensure tuning-up accuracy. In addition, the embodiment of the present disclosure may further save costs caused by the mechanical motor, the control component, or the like.

FIG. 1 is a flowchart of an example method for determining a target location of a single-slot collimating plate according to an embodiment of the present disclosure. A single-slot collimator including the single-slot collimating plate is disposed on an X-ray source side. The method shown in FIG. 1 is preferably performed by a control host of a CT system. The target position of the single-slot collimating plate can be determined by means of two instances of air scanning.

As shown in FIG. 1, the method includes the following steps.

Step 101: Acquire a first measurement signal collected based on the first time of air scanning when a single-slot collimating plate moves from a start location to a first location by a predetermined distance along a first direction of a Z-axis.

Herein, the Z-axis is a row arrangement direction of a detector array.

When the single-slot collimating plate moves from the start location to the first location by the predetermined distance along the first direction of the Z-axis, the CT system performs the first time of air scanning. The detector array of the CT system detects a measurement signal (referred to as a first measurement signal) during the first time of air scanning. The first measurement signal is determined by X-ray intensity detected in the first time of air scanning in rows on the Z-axis. For example, the X-ray intensity may be used to describe the first measurement signal, or a logarithm of the X-ray intensity may be used to describe the first measurement signal. In addition, the detector array sends the first measurement signal to the control host by using a transmission link such as a cable.

Step 102: Acquire a second measurement signal collected based on the second time of air scanning when the single-slot collimating plate moves from the start location to a second location by the predetermined distance along an opposite direction of the first direction.

Herein, the single-slot collimating plate returns from the first location to the start location. Further, when the single-slot collimating plate moves from the start location to the second location by the predetermined distance along the opposite direction of the first direction of the Z-axis, the CT system performs the second time of air scanning. The detector array detects a measurement signal (referred to as a second measurement signal) during the second time of air scanning. The second measurement signal is determined by X-ray intensity detected in the second time of air scanning in rows on the Z-axis. For example, the X-ray intensity may be used to describe the second measurement signal, or a logarithm of the X-ray intensity may be used to describe the second measurement signal. In addition, the detector array sends the second measurement signal to the control host by using a transmission link such as a cable.

Figure 2:
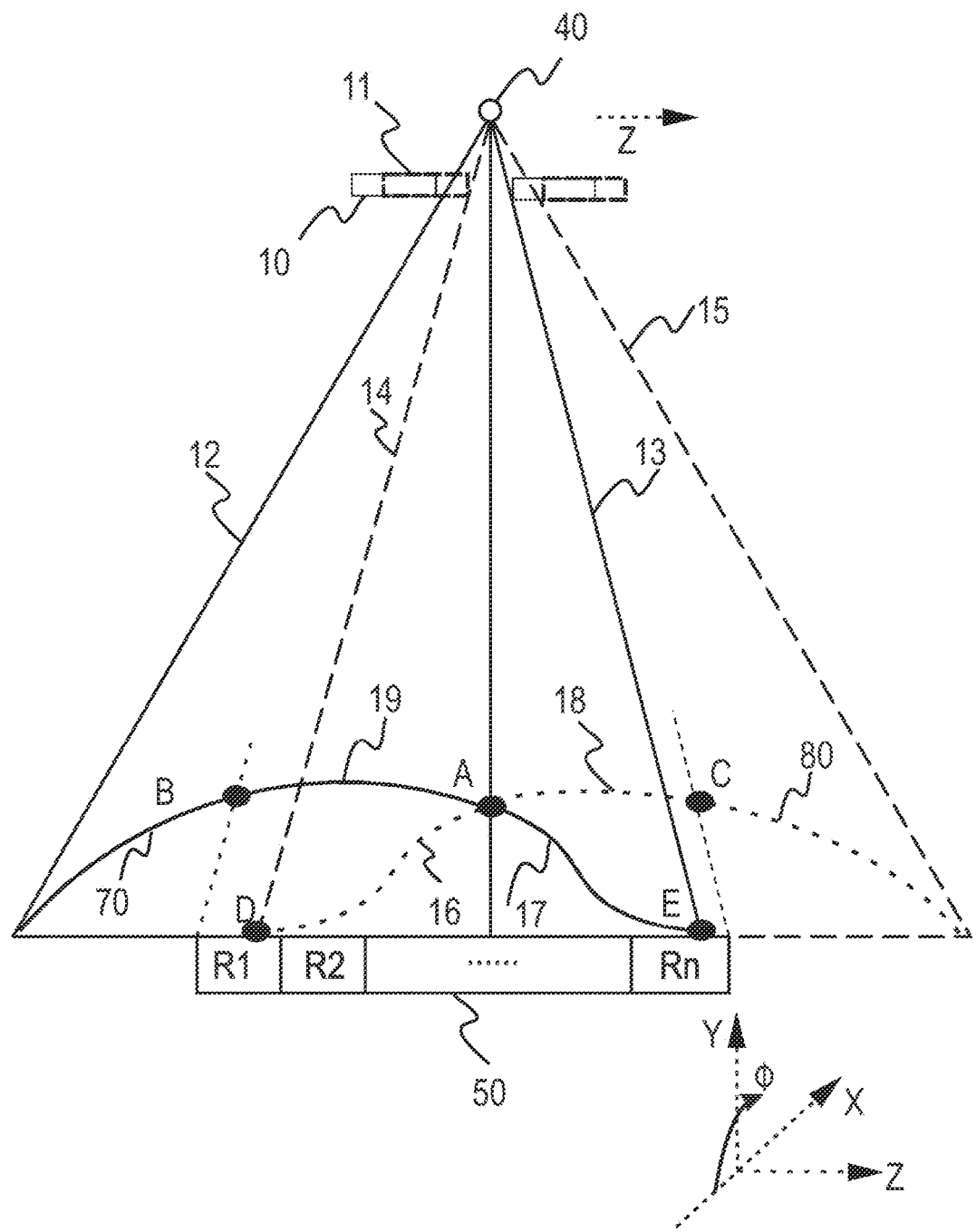
FIG. 2 is a schematic cross-sectional diagram of an example air scanning of CT in a Z-axis direction according to an embodiment of the present disclosure.

FIG. 2 is a schematic cross-sectional diagram of air scanning of CT in a Z-axis direction according to an embodiment of the present disclosure.

The single-slot collimating plate moves from the start location (initial) to a current location (initial−shift) by the predetermined distance (shift) along the reverse direction of the Z-axis shown in FIG. 2 (that is, the opposite direction of the arrow marked with Z in FIG. 2). Next, the CT system performs the first time of air scanning. Specifically, an X ray emitted from a focal point 40 undergoes a beam limiting action of a single-slot collimating plate 10 moving to the current location (initial−shift) to form a transmission range defined by an X ray 12 and an X ray 13. When a detector array 50 has enough rows in the Z-axis direction, the detector array 50 may detect a measurement signal identified by a complete solid line curve 70. However, since the detector array 50 typically has only a limited quantity of rows, the solid line curve 70 may not actually be fully detected. For example, as shown in FIG. 2, the detector array 50 that includes the first row R1, the second row R2, . . . , and the nth row Rn detects, in the transmission range, a measurement signal identified by a solid line curve BE. A point B is an intersection point between a line connecting a tail end of the first row R1 in the reverse direction of the Z-axis and the focal point 40 and the solid line curve 70, and a point E is an intersection point between the X ray 13 and the detector array 50. It can be seen that the solid line curve BE is a part of the solid line curve 70. The solid line curve BE is a measurement signal (the first measurement signal) detected by the detector array 50 for the first time of air scanning, and is determined by intensity of X-rays detected in each row in the Z-axis direction in the first time of air scanning.

Then, the single-slot collimating plate returns from the current location (initial−shift) to the start location (initial) and moves from the start location (initial) to the current location (initial+shift) by the same predetermined distance (shift) in the forward direction of the Z-axis as shown in FIG. 2 (i.e., the arrow direction identified by Z in FIG. 2). Next, the CT system performs the second time of air scanning. Specifically, an X ray emitted from a focal point 40 undergoes a beam limiting action of a single-slot collimating plate 11 moving to the current location (initial+shift) to form a transmission range defined by an X ray 14 and an X ray 15. When the detector array 50 has enough rows, the detector array 50 may detect a measurement signal identified by a complete dotted line curve 80. However, since the detector array 50 typically has only a limited quantity of rows, the dotted line curve 80 may not actually be fully detected. For example, as shown in FIG. 2, the detector array 50 that includes the first row R1, the second row R2, . . . , and the nth row Rn detects, in the transmission range, a measurement signal identified by a dotted line curve DC. A point C is an intersection point between a line connecting a tail end of the nth row Rn in the forward direction of the Z-axis and the focal point 40 and the dotted line curve 80, and a point D is an intersection point between the X ray 14 and the detector array 50. It can be seen that the dotted line curve DC is a part of the dotted line curve 80. The dotted line curve DC is a measurement signal (the second measurement signal) detected by the detector array 50 for the second time of air scanning, and is determined by intensity of X-rays detected in each row in the Z-axis direction in the second time of air scanning.

Step 103: Determine a combined measurement signal and a combined air calibration signal based on the first measurement signal and the second measurement signal.

Herein, the control host determines the combined measurement signal and the combined air calibration signal based on the first measurement signal and the second measurement signal.

In an embodiment, step 103 of determining a combined measurement signal and a combined air calibration signal based on the first measurement signal and the second measurement signal includes: determining a demarcation point between the first measurement signal and the second measurement signal; combining a first signal segment that is in the second measurement signal and that extends from the demarcation point along the first direction of the Z-axis with a second signal segment that is in the first measurement signal and that extends from the demarcation point along the opposite direction into the combined measurement signal; and combining a third signal segment that is in the first measurement signal and that extends from the demarcation point along the first direction of the Z-axis with a fourth signal segment that is in the second measurement signal and that extends from the demarcation point along the opposite direction into the combined air calibration signal. The demarcation point may be an intersection point between the first measurement signal and the second measurement signal, or may be a peripheral point of an intersection point between the first measurement signal and the second measurement signal.

Following the example in FIG. 2, the point A is an intersection point between the first measurement signal and the second measurement signal. The point A is used as a demarcation point between the first measurement signal and the second measurement signal.

A solid line AE included in the solid line curve BE is a second signal segment 17, and a dotted line DA included in the dotted line curve DC is a first signal segment 16. The first signal segment 16 and the second signal segment 17 are combined into a combined measurement signal.

Figure 3:
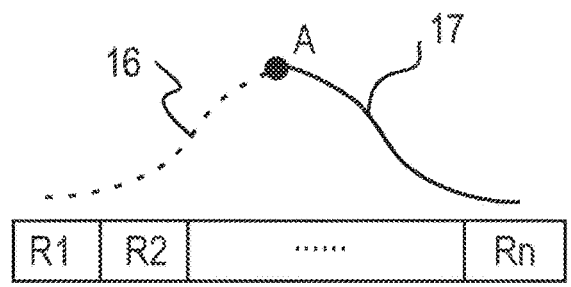
FIG. 3 is a schematic diagram of an example of combining to obtain a combined measurement signal according to an embodiment of the present disclosure.

FIG. 3 is a schematic diagram of combining to obtain a combined measurement signal according to an embodiment of the present disclosure. In FIG. 3, the first signal segment 16 and the second signal segment 17 form a combined curve by using the point A, that is, a combined measurement signal.

A solid line BA included in the solid line curve BE is a third signal segment 19, and a dotted line AC included in the dotted line curve DC is a fourth signal segment 18. The third signal segment 19 and the fourth signal segment 18 are combined into a combined air calibration signal.

Figure 4:
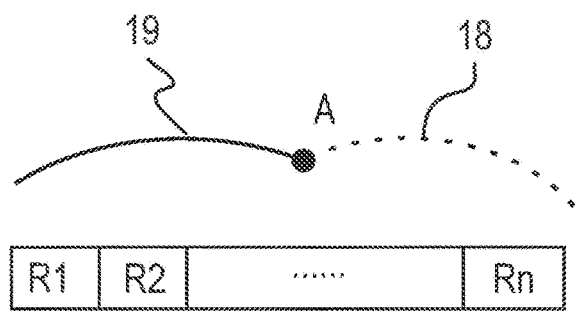
FIG. 4 is a schematic diagram of an example of combining to obtain a combined air calibration signal according to an embodiment of the present disclosure.

FIG. 4 is a schematic diagram of combining to obtain a combined air calibration signal according to an embodiment of the present disclosure. In FIG. 4, the third signal segment 19 and the fourth signal segment 18 form a combined curve by using the point A, that is, a combined air calibration signal.

Step 104: Calibrate the combined measurement signal by using the combined air calibration signal.

Herein, the control host calibrates the combined air calibration signal by using the combined measurement signal, to obtain the calibrated combined measurement signal.

Specifically, when both the first measurement signal and the second measurement signal are described by using logarithms of X-ray intensity detected in respective air scanning (that is, logarithm operation is performed on X-ray intensity detected in respective air scanning of both the first measurement signal and the second measurement signal), the combined air calibration signal may be subtracted from the combined measurement signal to obtain the calibrated combined air calibration signal. Alternatively, when both the first measurement signal and the second measurement signal are described by using X-ray intensity detected in respective air scanning (that is, logarithm operation is not performed on X-ray intensity detected in respective air scanning of both the first measurement signal and the second measurement signal), the combined measurement signal may be divided by the combined air calibration signal to obtain the calibrated combined air calibration signal.

Figure 5:
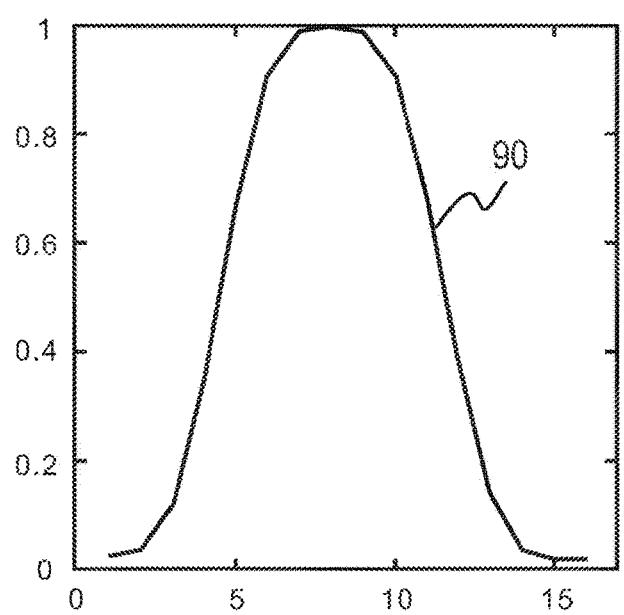
FIG. 5 is a schematic diagram of an example calibrated combined measurement signal according to an embodiment of the present disclosure.

FIG. 5 is a schematic diagram of a calibrated combined measurement signal according to an embodiment of the present disclosure. In FIG. 5, a calibrated combined measurement signal 90 is displayed in a coordinate system in which a serial number of a row is a horizontal axis and signal intensity is a vertical axis.

Step 105: Determine a target location of the single-slot collimating plate based on the calibrated combined measurement signal.

Herein, the control host may first determine a center of gravity of the calibrated combined measurement signal, and then determine the target location of the single-slot collimating plate based on the center of gravity. For a specific manner in which the control host determines the center of gravity of the calibrated combined measurement signal, references may be made to various center of gravity (COG) algorithms, which is not limited in the embodiment of the present disclosure.

Each detector in the detector array has a plurality of channels in a channel direction, where the channel direction is an arrangement direction of the channels in the detector array. The detector array is usually an arcuate detector array, so the channel direction is usually arcuate. For example, as shown in the lower right corner of FIG. 2, in a three-dimensional spatial rectangular coordinate system (X-Y-Z), the Z-axis direction is the arrangement direction of rows in the detector array, a channel direction Φ is located in an XY plane perpendicular to the Z-axis, and the channel direction Φ has an arcuate shape corresponding to an arcuate detector array.

The left channel group, the right channel group, and the middle channel group between the left channel group and the right channel group can be determined in advance along the channel direction.

For example, the left channel group, the right channel group, and the middle channel group may be determined based on the number sequence of the channels arranged in the channel direction. For example, assuming that the detector array has 768 channels in the channel direction, channel 1-channel 50 may be determined as the left channel group, channel 411-channel 460 are determined as the middle channel group, and channel 719-channel 768 are determined as the right channel group.

Examples of determining the channel group are illustrated in detail, a person skilled in the art may be aware that, the illustration described herein is exemplary, and is not intended to limit the protection scope of this embodiment manner of the present disclosure.

In an embodiment, a center of gravity of an average signal of each calibrated combined measurement signal detected by the middle channel group is determined, and a Z location offset of the single-slot collimating plate is determined based on the center of gravity. Specifically, a first average signal of a calibrated combined measurement signal of each channel in the middle channel group is determined; a center of gravity of the first average signal is determined; and a Z location offset of the single-slot collimating plate is determined based on the center of gravity of the first average signal. The center of gravity of the first average signal is in a coordinate system in which a serial number of a row is a horizontal axis and signal intensity of an X ray is a vertical axis.

For example, it is assumed that the middle channel group includes channel 411-channel 460. In this case, each channel in channel 411-channel 460 may separately acquire a calibrated combined measurement signal 90 shown in FIG. 5 (in the coordinate system in which the row number is the horizontal axis and the signal intensity is the vertical axis). That is, the middle channel group may acquire a total of 50 calibrated combined measurement signals 90 as shown in FIG. 5 (respectively obtained by using channel 411-channel 460). The average value of the 50 calibrated combined measurement signals 90 shown in FIG. 5 is the first average signal of the calibrated combined measurement signals of the channels in the middle channel group. Based on the center of gravity of the first average signal and a fixed parameter of the CT system (for example, a distance between the focal point and the single-slot collimating plate, a distance between the focal point and a rotation center (ISO), or an actual layer width of the detector array), the Z-location offset of the single-slot collimating plate can be determined.

It can be learned that, in this embodiment of the present disclosure, the Z location offset of the single-slot collimating plate can be conveniently determined by using the center of gravity of the first average signal formed by the middle channel group.

In an embodiment, a center of gravity of an average signal of the combined measurement signal detected by the left channel group is determined, a center of gravity of an average signal of the combined measurement signal detected by the right channel group is determined, and parallelism of the single-slot collimating plate is determined based on the two centers of gravity. The parallelism of the single-slot collimating plate reflects parallelism between emergent light of a collimator and a mechanical axis of the collimator.

In an embodiment, a second average signal of a calibrated combined measurement signal of each channel in the left channel group is determined; a center of gravity of the second average signal is determined; a third average signal of a calibrated combined measurement signal of each channel in the right channel group is determined; a center of gravity of the third average signal is determined; and parallelism of the single-slot collimating plate is determined based on the center of gravity of the second average signal and the center of gravity of the third average signal. Both the center of gravity of the second average signal and the center of gravity of the third average signal are in the coordinate system in which the serial number of the row is the horizontal axis and the signal intensity of the X ray is the vertical axis.

For example, it is assumed that the left channel group includes channel 1-channel 50, and the right channel group includes channel 719-channel 768. In this case, each channel in channel 1-channel 50 and channel 411-channel 460 may separately acquire a calibrated combined measurement signal 90 shown in FIG. 5 (in the coordinate system in which the row number is the horizontal axis and the signal intensity is the vertical axis). Specifically, the left channel group may acquire a total of 50 calibrated combined measurement signals 90 as shown in FIG. 5 (respectively obtained by using channel 1-channel 50). The right channel group may acquire a total of 50 calibrated combined measurement signals 90 as shown in FIG. 5 (respectively obtained by using channel 719-channel 768). The average value of the 50 combined measurement signals 90 acquired by the left channel group is a second average signal of the calibrated combined measurement signals of each channel in the left channel group. The average value of the 50 combined measurement signals 90 acquired by the right channel group is a third average signal of the calibrated combined measurement signals of each channel in the right channel group. Based on the center of gravity of the second average signal, the center of gravity of the third average signal, and the fixed parameter of the CT system (for example, the total quantity of channels, the maximum channel number in the left channel group, and the maximum channel number in the right channel group), parallelism of the single-slot collimating plate may be determined.

It can be learned that, in this embodiment of the present disclosure, the parallelism of the single-slot collimating plate can be conveniently determined by using the center of gravity of the second average signal formed by the left channel group and the center of gravity of the third average signal formed by the right channel group.

In an embodiment, curvature of the single-slot collimating plate is determined based on the center of gravity of the second average signal, the center of gravity of the third average signal, and the center of gravity of the first average signal. When the curvature is greater than a predetermined curvature threshold, alarm information indicating to replace the single-slot collimating plate is sent. The center of gravity of the first average signal, the center of gravity of the second average signal, and the center of gravity of the third average signal are all located in the coordinate system in which the serial number of the row is the horizontal axis and the signal intensity of the X ray is the vertical axis.

For example, it is assumed that the middle channel group includes channel 411-channel 460, the left channel group includes channel 1-channel 50, and the right channel group includes channel 719-channel 768. In this case, each channel in the middle channel group, the left channel group, and the right channel group may separately acquire a calibrated combined measurement signal 90 shown in FIG. 5 (in the coordinate system in which the row number is the horizontal axis and the signal intensity is the vertical axis).

The middle channel group may acquire a total of 50 calibrated combined measurement signals 90 as shown in FIG. 5 (respectively obtained by using channel 411-channel 460). The average value of the 50 calibrated combined measurement signals 90 acquired by the middle channel group as shown in FIG. 5 is the first average signal of the calibrated combined measurement signals of the channels in the middle channel group. The left channel group may acquire a total of 50 calibrated combined measurement signals 90 as shown in FIG. 5 (respectively obtained by using channel 1—channel 50). The average value of the 50 combined measurement signals 90 acquired by the left channel group is a second average signal of the calibrated combined measurement signals of each channel in the left channel group. The right channel group may acquire a total of 50 calibrated combined measurement signals 90 as shown in FIG. 5 (respectively obtained by using channel 719-channel 768). The average value of the 50 combined measurement signals 90 acquired by the right channel group is a third average signal of the calibrated combined measurement signals of each channel in the right channel group.

The curvature of the single-slot collimating plate may be determined based on the center of gravity of the first average signal, the center of gravity of the second average signal, the center of gravity of the third average signal, and the fixed parameter of the CT system (for example, a distance between the focal point and the single-slot collimating plate, a distance between the focal point and the ISO, an actual layer width of the detector array, the total quantity of channels, the maximum channel number in the left channel group, and the maximum channel number in a right channel group).

It can be learned that, in this embodiment of the present disclosure, the curvature of the single-slot collimating plate can be conveniently determined based on the center of gravity of the second average signal, the center of gravity of the third average signal, and the center of gravity of the first average signal, and an alarm is given when the curvature exceeds the threshold.

The following describes an embodiment of the present disclosure with reference to a specific algorithm.

In the channel direction, the left channel group L, the right channel group R, and the middle channel group M located between the left channel group L and the right channel group R are determined. For example, L=719:768; M=411:460; R=1:50. That is, the left channel group L includes channel 719-channel 778, the right channel group R includes channel 1-channel 50, and the middle channel group M includes channel 411-channel 460.

First, the single-slot collimating plate moves by a predetermined distance shift in a direction (for example, the reverse direction of the Z-axis) of the Z-axis from the start location z-initial on the Z-axis, arrives at the location initial-shift, and performs the first time of air scanning. Measurement data acquired by the detector array is $S_-(m, q, n)$, where m is a channel number, q is a row number, and n is a reading.

Then, the single-slot collimating plate returns from the upright location to the start location Z-initial, moves by the same predetermined distance shift in another direction of the Z-axis (for example, the forward direction of Z-axis), arrives at the location initial+shift, and performs the second time of air scanning. Measurement data acquired by the detector array is $S_+(m,q,n)$. Before the second time of air scanning, the measurement data $S_-(m,q,n)$ acquired during the first time of air scanning may be pre-checked, so as to ensure that the start location z-initial is acceptable.

Then, $S_+(m,q,n)$ and $S_-(m,q,n)$ are combined to respectively obtain a combined measurement signal $data_{combine}(m, q,n)$ and a combined air calibration signal $aircal_{combine}(m, q,n)$. where:

$$aircal_{combine}(m, q, n) = \begin{cases} S_-(m, q, n) & 1 \le q \le q' \\ S_+(m, q, n) & q' + 1 \le q \le N \end{cases} \quad (1)$$

$$data_{combine}(m, q, n) = \begin{cases} S_+(m, q, n) & 1 \le q \le q' \\ S_-(m, q, n) & q' + 1 \le q \le N \end{cases} \quad (2)$$

q' is a demarcation point between the measurement data acquired during the first time of air scanning and the measurement data acquired by the second time of air scanning, and q' meets the following relationship:

$$\frac{1}{N_r \times N_M} \sum_{n=1}^{N_r} \sum_{m \in M} S_-(m, q', n) \leq \qquad (3)$$

$$\frac{1}{N_r \times N_M} \sum_{n=1}^{N_r} \sum_{m \in M} S_+(m, q', n)$$

$$\frac{1}{N_r \times N_M} \sum_{n=1}^{N_r} \sum_{m \in M} S_-(m, q'+1, n) \geq \qquad (4)$$

$$\frac{1}{N_r \times N_M} \sum_{n=1}^{N_r} \sum_{m \in M} S_+(m, q'+1, n)$$

where $N_r$ is the quantity of readings, and $N_M$ is the quantity of channels included in the middle group M.

Then, the combined measurement signal data$_{combine}$ (m, q, n) is calibrated by using the combined air calibration signal aircal$_{combine}$(m, q, n) and is averaged on the reading n to obtain the calibrated combined measurement signal $S_{comb}$'(m, q). When $S_+$(m, q, n) and $S_-$(m, qn) are respectively represented by logarithms of X-ray intensity detected in respective air scanning, $S_{comb}$'(m, q) is the average value of data$_{combine}$(m, q, n)–air cal$_{combine}$(m, q, n) on the reading n. When $S_+$(m, q, n) and $S_-$(m, q, n) are respectively represented by X-ray intensity detected in respective air scanning, data$_{combine}$(m, q, n)–aircal$_{combine}$(m, q, n) is the average value on the reading n.

Then, $S_{comb}$'(m, q) is averaged according to the channel quantities in respective channel groups, to separately calculate respective average signals $S^{L,M,R}_q$ a of the left channel group L, the right channel group R, and the middle channel group M, where:

$$S_q^{L,M,R} = \frac{1}{N_{L,M,R}} \sum_{m \in L,M,R} S'_{comb}(m, q) \qquad (5)$$

$N_{L,M,R}$ indicates the quantities of channels in the left channel group L, the right channel $q_{COG}^{L,M,R}$ group R, and the middle channel group M.

Then, a COG algorithm is used to separately calculate respective centers of gravity q COG of the left channel group L, the right channel group R, and the middle channel group M, where:

$$q_{COG}^{L,M,R} = \frac{\sum (q - Q_c) S_q^{L,M,R}}{\sum S_q^{L,M,R}} \qquad (6)$$

$Q_C$ is the number of central row.
The optimal Z location offset $Z_{optimal}$ may then be calculated, where:

$$Z_{optimal}^{L,M,R} = z\text{-initial} - q_{COG}^{L,M,R} \times w \times \frac{dFc}{dF} \qquad (7)$$

$$Z_{optimal} = Z_{optimal}^M \qquad (8)$$

w is the actual layer width of the detector array, dFc is the distance between the focal point and the single-slot collimating plate, dF is the distance between the focal point and the rotation center (ISO), and z-initial is the start location on the Z axis.

In addition, parallelism $\Delta Z_{equal}^{Parallel}$ may also be calculated, where:

$$\Delta Z_{equal}^{Parallel} = (Z_{optimal}^L - Z_{optimal}^R) \times R_{ChannelGroup} \qquad (9)$$

$$R_{ChannelGroup} = M'/(m_u^L - m_u^R) \qquad (10)$$

M' is the total quantity of channels, $m_u^L$ is the maximum channel number in the left channel group L, and $m_u^R$ is the maximum channel number in the right channel group R.

In addition, $\Delta Z_{equal}^{Parallel}$ should meet the following conditions:

$$|\Delta Z_{equal}^{Parallel}| \leq \Delta Z^{Parallel} \qquad (11)$$

$\Delta Z^{Parallel}$ is the parallelism threshold value of the single-slot collimating plate.

Finally, the curvature $$\left| \frac{(Z_{optimal}^L + Z_{optimal}^R - 2 \times Z_{optimal}^M)}{2} \right|$$

may be calculated.

In addition, the calculated curvature should meet the following conditions:

$$\left| \frac{(Z_{optimal}^L + Z_{optimal}^R - 2 \times Z_{optimal}^M)}{2} \right| \leq \Delta Z^{Curv} \qquad (12)$$

$\Delta Z^{Curv}$ is a threshold value of the curvature.

It can be learned that, compared with the prior art in which multiple air measurement are required to tune up the location of the slot, in this embodiment of the present disclosure, tuning up of the slot can be completed by using signal combination through only two times of air measurement, which is more efficient, simpler, and convenient. In addition, because a quantity of times of air scanning is significantly reduced, costs such as a mechanical motor or a control component can be further reduced in the embodiment of the present disclosure.

Figure 6:
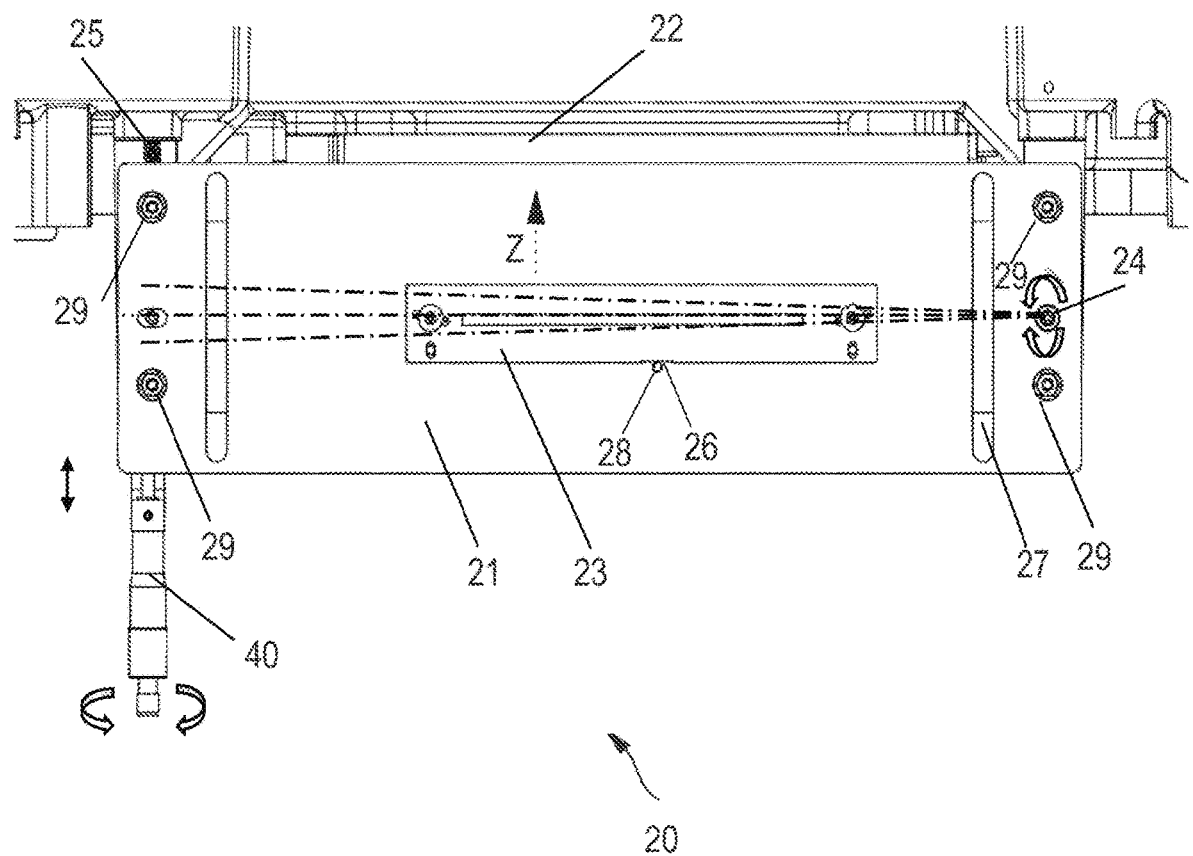
FIG. 6 is a first schematic diagram of an example of tuning up a target location of a single-slot collimating plate in a collimator assembly according to an embodiment of the present disclosure.

Based on the foregoing description, an embodiment of the present disclosure further proposes a collimator assembly adapted to a tuned-up location. FIG. 6 is a first schematic diagram of tuning up a target location of a single-slot collimating plate in a collimator assembly according to an embodiment of the present disclosure. The location of the collimating plate can be conveniently tuned up without using a mechanical motor or a control component.

In FIG. 6, a collimator assembly 20 includes:
 a frame 21, adapted to be disposed on a rotating carrier 22;
 a single-slot collimating plate 23, disposed in the frame 21;
 a rotational fulcrum 24, fixed at a first end of the frame 21; and
 a spring 25, disposed between an opposite end of the first end of the frame 21 and the rotating carrier 22;
 where the single-slot collimating plate 23 includes a recess 26, and the frame 21 has a rotation degree of freedom around the rotational fulcrum 24; the single-slot collimating plate 23 is adapted to be moved to a target location based on a rotation process of the frame 21 around the rotational fulcrum 24 or a process of filling the recess 26 with a gasket, where the target location is determined by using the method for determining a target location of a single-slot collimating plate as described above.

The rotating carrier 22 may be implemented as a flange-shaped structural component, and provides fixed support for a rotating component such as a ball tube, a collimator assembly, and a detector. The single-slot collimating plate 23 is preferably made of an X-ray shielding material of high-density metal such as a tungsten alloy.

After a control host determines a Z location offset and a target value of parallelism of the single-slot collimating plate 23 based on the method for determining a target location of a single-slot collimating plate shown in FIG. 1, the rotation amount of the frame 21 around the rotational fulcrum 24 may be tuned up by using a micrometer caliper 40 coupled to a first end of the frame 21, so that the parallelism of the single-slot collimating plate 23 meets the target value. After the parallelism of the single-slot collimating plate 23 reaches the target value, a gasket of an appropriate specification is filled in the recess 26, so that a Z location of the single-slot collimating plate 23 meets the Z location offset. After the location of the single-slot collimating plate 23 is tuned up, four fastening bolts 29 on the frame 21 may be used, so that the frame 21 is fixed to the rotating carrier 22. Preferably, a locating pin 28 is disposed at a location on the frame 21 that is opposite to the recess opening to fix the gasket in the recess 26.

Preferably, in the frame 21, two parallel handles 27 are disposed at two ends of the single-slot collimating plate 23 along the Z-axis direction. A user may conveniently move the frame 21 by using the two handles 27.

Figure 7:
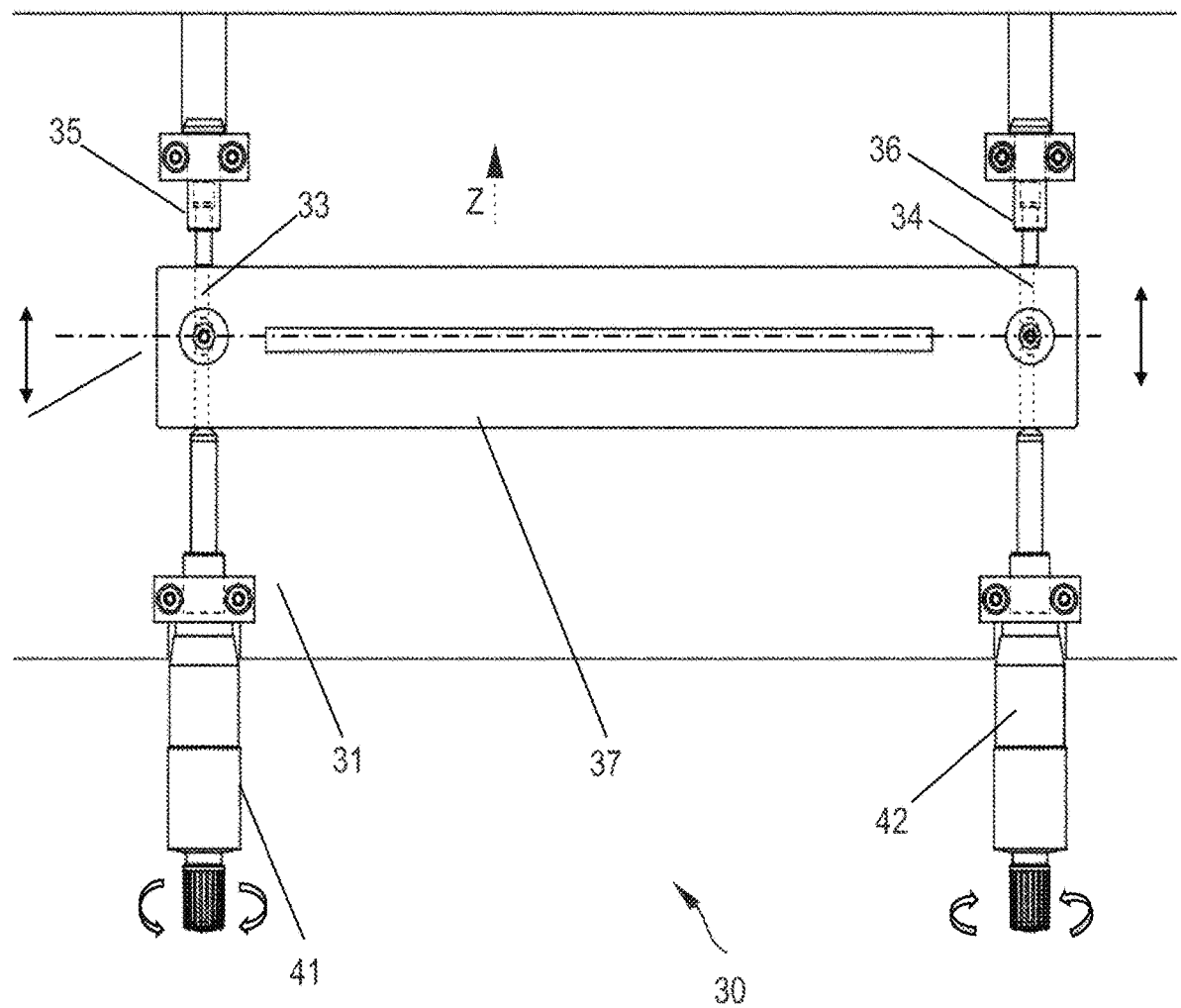
FIG. 7 is a first schematic diagram of an example of tuning up a target location of a single-slot collimating plate in a collimator assembly according to an embodiment of the present disclosure.

Based on the foregoing description, an embodiment of the present disclosure further proposes another collimator assembly adapted to a tuned-up location. FIG. 7 is a second schematic diagram of tuning up a target location of a single-slot collimating plate in a collimator assembly according to an embodiment of the present disclosure. The location of the slot may be tuned up without using a mechanical motor or a control component.

As shown in FIG. 7, a collimator assembly 30 includes:
- a frame 31, adapted to be arranged on a rotating carrier, the frame 31 being arranged with a first slot 33 and a second slot 34 arranged in parallel along a Z-axis direction;
- a single-slot collimating plate 37, disposed in the frame 31;
- a first spring 35, where a first end of the first spring 35 is fixed to the frame 31, and a second end of the first spring 35 is in contact with a sidewall of the single-slot collimating plate 37; and
- a second spring 36, where a first end of the second spring 36 is fixed to the frame 31, and a second end of the second spring 36 is in contact with the sidewall;
- where a first end of the single-slot collimating plate 37 has a moving degree of freedom along the first slot 33, and an opposite end of the first end of the single-slot collimating plate 37 has a moving degree of freedom along the second slot 34; and the single-slot collimating plate 37 is adapted to move to a target location base on combined movement of the first end of the single-slot collimating plate 37 along the first slot 33 and the opposite end of the first end of the single-slot collimating plate 37 along the second slot 34, movement of the first end of the single-slot collimating plate 37 along the first slot 33, or movement of the opposite end of the first end of the single-slot collimating plate 37 along the second slot 34, where the target location is determined by using the above method for determining a target location of a single-slot collimating plate.

The frame 31 may be disposed on the rotating carrier. The rotating carrier may be implemented as a flange-shaped structural component, and provides fixed support for a rotating component such as a ball tube, a collimator assembly, and a detector.

Example 1: When the control host determines the Z location offset and the target value of the parallelism of the single-slot collimating plate 37 based on the method for determining a target location of a single-slot collimating plate shown in FIG. 1, and the user finds that current parallelism of the single-slot collimating plate 37 is equal to the target value, the user synchronously tunes up a first micrometer caliper 41 coupled to a first end of the single-slot collimating plate 37 and a second micrometer caliper 42 coupled to a second end of the single-slot collimating plate 37, so that the single-slot collimating plate 37 keeps moving in the Z direction with the parallelism, and the Z location to which the single-slot collimating plate 37 moves meets the Z location offset.

Example 2: When the control host determines the Z location offset and the target value of the parallelism of the single-slot collimating plate 37 based on the method for determining a target location of a single-slot collimating plate shown in FIG. 1, and the user finds that current parallelism of the single-slot collimating plate 37 is not equal to the target value, the user may simultaneously tune up a first micrometer caliper 41 coupled to a first end of the single-slot collimating plate 37 and a second micrometer caliper 42 coupled to a second end of the single-slot collimating plate 37, so that the single-slot collimating plate 37 reaches the parallelism and moves in the Z direction, and the Z location to which the single-slot collimating plate 37 moves meets the Z location offset.

Example 3: When the control host determines the Z location offset and the target value of the parallelism of the single-slot collimating plate 37 based on the method for determining a target location of a single-slot collimating plate shown in FIG. 1, and the user finds that current parallelism of the single-slot collimating plate 37 is not equal to the target value, the user may separately tune up a first micrometer caliper 41 coupled to a first end of the single-slot collimating plate 37 or separately tune up a second micrometer caliper 42 coupled to a second end of the single-slot collimating plate 37, so that the single-slot collimating plate 37 reaches the parallelism and moves in the Z direction, and the Z location to which the single-slot collimating plate 37 moves meets the Z location offset.

Typical structures of the single-slot collimating plate are illustrated in detail, a person skilled in the art may be aware that, the illustration described herein is merely exemplary, and is not intended to limit the protection scope of this embodiment manner of the present disclosure.

Based on the foregoing description, an embodiment of the present disclosure further provides an apparatus for determining a target location of a single-slot collimating plate.

Figure 8:
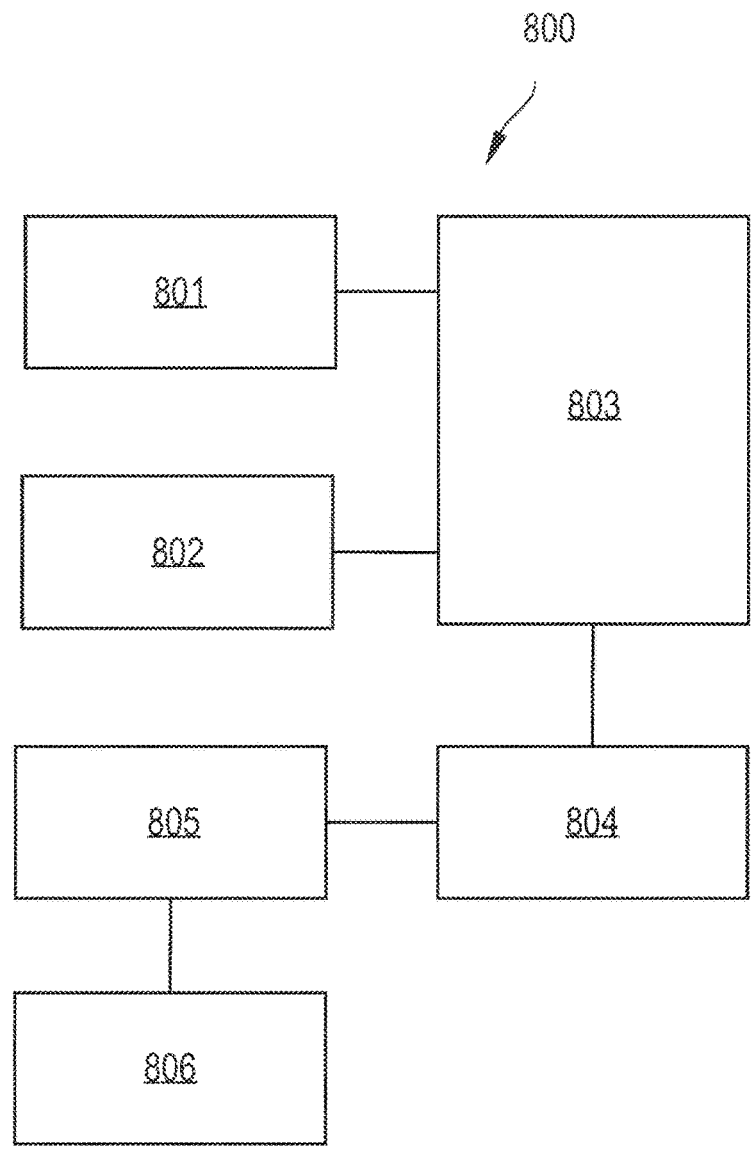
FIG. 8 is a structural diagram of an example apparatus for determining a target location of a single-slot collimating plate according to an embodiment of the present disclosure.

FIG. 8 is a structural diagram of an apparatus for determining a target location of a single-slot collimating plate according to an embodiment of the present disclosure.

As shown in FIG. 8, an apparatus 800 includes:
- a first acquiring module 801, configured to acquire a first measurement signal collected based on the first time of air scanning when a single-slot collimating plate moves from a start location to a first location by a predetermined distance along a first direction of a Z-axis;
- a second acquiring module 802, configured to acquire a second measurement signal collected based on the second time of air scanning when the single-slot collimating plate moves from the start location to a second location by the predetermined distance along an opposite direction of the first direction;

a first determining module 803, configured to determine a combined measurement signal and a combined air calibration signal based on the first measurement signal and the second measurement signal;

a calibration module 804, configured to calibrate the combined measurement signal by using the combined air calibration signal; and a second determining module 805, configured to determine a target location of the single-slot collimating plate based on the calibrated combined measurement signal.

In an embodiment, the first determining module 803 is configured to: determine a demarcation point between the first measurement signal and the second measurement signal; combine a first signal segment that is in the second measurement signal and that extends from the demarcation point along the first direction of the Z-axis with a second signal segment that is in the first measurement signal and that extends from the demarcation point along the opposite direction into the combined measurement signal; and combine a third signal segment that is in the first measurement signal and that extends from the demarcation point along the first direction of the Z-axis with a fourth signal segment that is in the second measurement signal and that extends from the demarcation point along the opposite direction into the combined air calibration signal.

In an embodiment, the second determining module 805 is configured to: determine a center of gravity of the calibrated combined measurement signal, and determine the target location of the single-slot collimating plate based on the center of gravity.

In an embodiment, the second determining module 805 is configured to: determine a left channel group, a right channel group, and a middle channel group between the left channel group and the right channel group based on a channel number sequence; determine a first average signal of a calibrated combined measurement signal of each channel in the middle channel group; determine a center of gravity of the first average signal; and determine a Z-location offset of the single-slot collimating plate based on the center of gravity of the first average signal.

In an embodiment, the second determining module 805 is further configured to: determine a second average signal of a calibrated combined measurement signal of each channel in the left channel group; determine a center of gravity of the second average signal; determine a third average signal of a calibrated combined measurement signal of each channel in the right channel group; determine a center of gravity of the third average signal; and determine parallelism of the single-slot collimating plate based on the center of gravity of the second average signal and the center of gravity of the third average signal.

In an embodiment, the second determining module 805 is further configured to determine curvature of the single-slot collimating plate based on the center of gravity of the second average signal, the center of gravity of the third average signal, and the center of gravity of the first average signal.

In an embodiment, the apparatus 800 further includes an alarm module 806, configured to: when the curvature is greater than a predetermined curvature threshold, send alarm information indicating to replace the single-slot collimating plate.

Based on the foregoing description, an embodiment of the present disclosure further provides a control host of a CT system.

Figure 9:
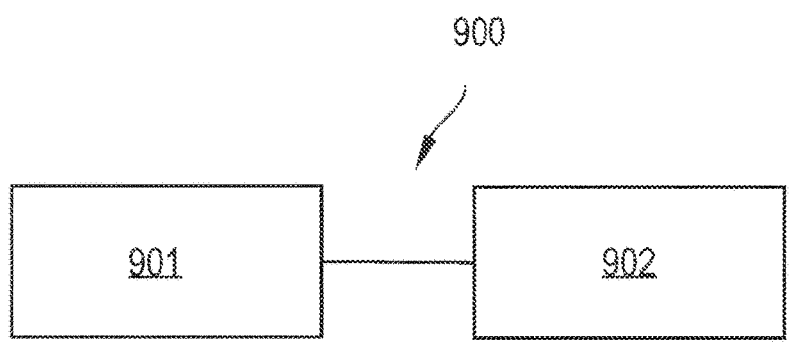
FIG. 9 is a structural diagram of an example control host of a CT system according to an embodiment of the present disclosure.

FIG. 9 is a structural diagram of a control host of a CT system according to an embodiment of the present disclosure.

As shown in FIG. 9, a control host 900 includes a memory 901 and a processor 902, where the memory 901 stores an application program capable of being executed by the processor 902, so that the processor 902 executes the method for determining a target location of a single-slot collimating plate.

The memory 901 may be specifically implemented as a plurality of storage media such as an electrically erasable programmable read-only memory (EEPROM), a flash memory, and a programmable program read-only memory (PROM). The processor 902 may be implemented as one or more central processing units or one or more field programmable gate arrays, where the field programmable gate array is integrated into one or more central processing units. Specifically, the central processing unit or the central processing unit core may be implemented as a CPU, an MCU, a DSP, or the like.

Not all steps and modules in the procedures and the structural diagrams are necessary, and some steps or modules may be omitted according to an actual need. An execution sequence of the steps is not fixed and may be tuned up according to needs. Division of the modules is merely functional division for ease of description. During actual embodiment, one module may be implemented separately by a plurality of modules, and functions of the plurality of modules may alternatively be implemented by the same module. The modules may be located in the same device or in different devices.

Hardware modules in the foregoing embodiments may be implemented in a mechanical manner or an electronic manner. For example, a hardware module may include a specially designed permanent circuit or logic device (such as a dedicated processor like an FPGA or an ASIC) for performing a specific operation. The hardware module may also include a programmable logic device or circuit (such as a general purpose processor or another programmable processor) that is temporarily configured by software to perform a specific operation. Whether the hardware module is specifically implemented in the mechanical manner, by using a dedicated permanent circuit, or by using a temporarily configured circuit (configured using software) may be determined according to costs and time considerations.

The present disclosure further provides a machine readable storage medium for storing instructions for causing a machine to execute the method described herein. Specifically, a system or an apparatus equipped with a storage medium may be provided. Software program code for implementing a function in any one of the foregoing embodiments is stored in the storage medium, and a computer (or a CPU or an MPU) of the system or apparatus reads and executes program code stored in the storage medium. In addition, an operating system operated on a computer or the like may be enabled to complete some or all actual operations by using a program code-based instruction. The program code read from the storage medium may be written into a memory disposed in an extension board inserted into the computer or into a memory disposed in an extension unit connected to the computer. Subsequently, a program code-based instruction enables a CPU installed on the extension board or the extension unit to perform some and all actual operations, so as to implement a function of any one of the foregoing embodiments.

The storage medium embodiment for providing program code includes a floppy disk, a hard disk, a magneto-optical disk, an optical disc (such as a CD-ROM, a CD-R, a CD-RW, a DVD-ROM, a DVD-RAM, a DVD-RW, and a DVD+RW), a magnetic tape, a non-volatile memory card, and a ROM. Alternatively, program code may be downloaded from a server computer via a communication network.

The foregoing descriptions are merely preferred embodiments of the present disclosure, are not intended to limit the protection scope of the present disclosure. A person skilled in the art may make various modifications and changes to this disclosure. Any modification, equivalent replacement, or improvement made without departing from the spirit and principle of this application shall fall within the protection scope of this disclosure.

The invention claimed is:

1. A method for determining a target location of a single-slot collimating plate, comprising:
   acquiring a first measurement signal that is collected based on a first time of air scanning when a single-slot collimating plate moves from a start location to a first location by a predetermined distance along a first direction;
   acquiring a second measurement signal that is collected based on a second time of air scanning when the single-slot collimating plate moves from the start location to a second location by the predetermined distance along an opposite direction to the first direction;
   determining a combined measurement signal and a combined air calibration signal based on the first measurement signal and the second measurement signal;
   calibrating the combined measurement signal using the combined air calibration signal; and
   determining a target location of the single-slot collimating plate based on the calibrated combined measurement signal.

2. The method according to claim 1, wherein the act of determining the combined measurement signal and the combined air calibration signal based on the first measurement signal and the second measurement signal comprises:
   determining a demarcation point between the first measurement signal and the second measurement signal;
   combining a first signal segment that is in the second measurement signal and extends from the demarcation point along the first direction, with a second signal segment that is in the first measurement signal and extends from the demarcation point along the opposite direction to the first direction into the combined measurement signal; and
   combining a third signal segment that is in the first measurement signal and extends from the demarcation point along the first direction, with a fourth signal segment that is in the second measurement signal and extends from the demarcation point along the opposite direction to the first direction into the combined air calibration signal.

3. The method according to claim 1, wherein the act of determining the target location of the single-slot collimating plate based on the calibrated combined measurement signal comprises:
   determining a center of gravity of the calibrated combined measurement signal; and
   determining the target location of the single-slot collimating plate based on the center of gravity.

4. The method according to claim 3, wherein;
   the act of determining the center of gravity of the calibrated combined measurement signal comprises:
      determining a left channel group, a right channel group, and a middle channel group between the left channel group and the right channel group, based on a channel number sequence;
      determining a first average signal of a calibrated combined measurement signal of each channel in the middle channel group;
      determining a center of gravity of the first average signal; and
      the act of determining the target location of the single-slot collimating plate based on the center of gravity comprises:
         determining an offset of the single-slot collimating plate based on the center of gravity of the first average signal.

5. The method according to claim 4, wherein;
   the act of determining the center of gravity of the calibrated combined measurement signal further comprises:
      determining a second average signal of a calibrated combined measurement signal of each channel in the left channel group;
      determining a center of gravity of the second average signal;
      determining a third average signal of a calibrated combined measurement signal of each channel in the right channel group; and
      determining a center of gravity of the third average signal; and
   the act of determining the target location of the single-slot collimating plate based on the center of gravity further comprises:
      determining parallelism of the single-slot collimating plate based on the center of gravity of the second average signal and the center of gravity of the third average signal.

6. The method according to claim 5, further comprising:
   determining a curvature of the single-slot collimating plate based on the center of gravity of the second average signal, the center of gravity of the third average signal, and the center of gravity of the first average signal; and
   when the curvature is greater than a predetermined curvature threshold, sending alarm information indicating a replacement of the single-slot collimating plate.

7. An apparatus for determining a target location of a single-slot collimating plate, comprising:
   first acquiring circuitry configured to acquire a first measurement signal that is collected based on a first time of air scanning when a single-slot collimating plate moves from a start location to a first location by a predetermined distance along a first direction;
   second acquiring circuitry configured to acquire a second measurement signal that is collected based on a second time of air scanning when the single-slot collimating plate moves from the start location to a second location by the predetermined distance along an opposite direction to the first direction;
   first determining circuitry configured to determine a combined measurement signal and a combined air calibration signal based on the first measurement signal and the second measurement signal;

calibration circuitry configured to calibrate the combined measurement signal using the combined air calibration signal; and second determining circuitry configured to determine a target location of the single-slot collimating plate based on the calibrated combined measurement signal.

8. The apparatus according to claim 7, wherein;
the first determining circuitry is configured to:
  determine a demarcation point between the first measurement signal and the second measurement signal;
  combine a first signal segment that is in the second measurement signal and that extends from the demarcation point along the first direction, with a second signal segment that is in the first measurement signal and that extends from the demarcation point along the opposite direction into the combined measurement signal; and
  combine a third signal segment that is in the first measurement signal and that extends from the demarcation point along the first direction, with a fourth signal segment that is in the second measurement signal and that extends from the demarcation point along the opposite direction into the combined air calibration signal.

9. The apparatus according to claim 7, wherein:
the second determining circuitry is configured to determine a center of gravity of the calibrated combined measurement signal, and to determine the target location of the single-slot collimating plate based on the center of gravity.

10. The apparatus according to claim 9, wherein;
the second determining circuitry is configured to:
  determine a left channel group, a right channel group, and a middle channel group between the left channel group and the right channel group, based on a channel number sequence;
  determine a first average signal of a calibrated combined measurement signal of each channel in the middle channel group;
  determine a center of gravity of the first average signal; and
  determine an offset of the single-slot collimating plate based on the center of gravity of the first average signal.

11. The apparatus according to claim 10, wherein:
the second determining circuitry is further configured to:
  determine a second average signal of a calibrated combined measurement signal of each channel in the left channel group;
  determine a center of gravity of the second average signal;
  determine a third average signal of a calibrated combined measurement signal of each channel in the right channel group;
  determine a center of gravity of the third average signal; and
  determine parallelism of the single-slot collimating plate based on the center of gravity of the second average signal and the center of gravity of the third average signal.

12. The apparatus according to claim 11, wherein;
the second determining module is further configured to determine a curvature of the single-slot collimating plate based on the center of gravity of the second average signal, the center of gravity of the third average signal, and the center of gravity of the first average signal; and the apparatus further comprises:
  alarm circuitry configured to, when the curvature is greater than a predetermined curvature threshold, send alarm information indicating a replacement of the single-slot collimating plate.

13. A collimator assembly, comprising:
a frame configured to be disposed on a rotating carrier;
a single-slot collimating plate disposed in the frame;
a rotational fulcrum fixed at a first end of the frame; and
a spring disposed between an opposite end to the first end of the frame and the rotating carrier,
wherein the single-slot collimating plate comprises a recess, and the frame has a rotational degree of freedom around the rotational fulcrum,
wherein the single-slot collimating plate is configured to be moved to a target location based on a rotation of the frame around the rotational fulcrum, or a filling of the recess with a gasket, and
wherein the target location is determined by:
  acquiring a first measurement signal that is collected based on a first time of air scanning when a single-slot collimating plate moves from a start location to a first location by a predetermined distance along a first direction;
  acquiring a second measurement signal that is collected based on a second time of air scanning when the single-slot collimating plate moves from the start location to a second location by the predetermined distance along an opposite direction to the first direction;
  determining a combined measurement signal and a combined air calibration signal based on the first measurement signal and the second measurement signal;
  calibrating the combined measurement signal using the combined air calibration signal; and
  determining a target location of the single-slot collimating plate based on the calibrated combined measurement signal.

14. A collimator assembly, comprising:
a frame on which a first slot and a second slot that are arranged in parallel along a first direction are disposed;
a single-slot collimating plate disposed in the frame;
a first spring,
wherein a first end of the first spring is fixed to the frame, and
wherein a second end of the first spring is in contact with a sidewall of the single-slot collimating plate; and
a second spring,
wherein a first end of the second spring is fixed to the frame, and
wherein a second end of the second spring is in contact with the sidewall,
wherein a first end of the single-slot collimating plate has a moving degree of freedom along the first slot, and an opposite end to the first end of the single-slot collimating plate has a moving degree of freedom along the second slot, and
wherein the single-slot collimating plate is configured to move to a target location based on combined movement of the first end of the single-slot collimating plate along the first slot and the opposite end to the first end of the single-slot collimating plate along the second slot, movement of the first end of the single-slot collimating plate along the first slot, or movement of the opposite end of the first end of the single-slot collimating plate along the second slot, wherein the target location is determined by:
  acquiring a first measurement signal that is collected based on a first time of air scanning when a single-slot collimating plate moves from a start location to a first location by a predetermined distance along a first direction;
  acquiring a second measurement signal that is collected based on a second time of air scanning when the single-slot collimating plate moves from the start location to a second location by the predetermined distance along an opposite direction to the first direction;
  determining a combined measurement signal and a combined air calibration signal based on the first measurement signal and the second measurement signal:
  calibrating the combined measurement signal using the combined air calibration signal; and
  determining a target location of the single-slot collimating plate based on the calibrated combined measurement signal.

15. A non-transitory computer readable medium having instructions stored thereon that, when executed by a processor, cause the processor to determine a target location of a single-slot collimating plate by:
  acquiring a first measurement signal that is collected based on a first time of air scanning when a single-slot collimating plate moves from a start location to a first location by a predetermined distance along a first direction;
  acquiring a second measurement signal that is collected based on a second time of air scanning when the single-slot collimating plate moves from the start location to a second location by the predetermined distance along an opposite direction to the first direction;
  determining a combined measurement signal and a combined air calibration signal based on the first measurement signal and the second measurement signal;
  calibrating the combined measurement signal using the combined air calibration signal; and
  determining a target location of the single-slot collimating plate based on the calibrated combined measurement signal.

* * * * *